(12) United States Patent
Li et al.

(10) Patent No.: US 10,083,372 B2
(45) Date of Patent: Sep. 25, 2018

(54) ULTRASOUND DIAGNOSIS APPARATUS, IMAGE PROCESSING APPARATUS AND IMAGE PROCESSING METHOD

(71) Applicant: Toshiba Medical Systems Corporation, Otawara-shi (JP)

(72) Inventors: Guang Li, ChaoYang (CN); Hiroki Yoshiara, Omiya (JP); Lingying Chen, ChaoYang (CN); Zhe Tang, ChaoYang (CN)

(73) Assignee: Toshiba Medical Systems Corporation, Otawara-shi (JP)

( * ) Notice: Subject to any disclaimer, the term of this patent is extended or adjusted under 35 U.S.C. 154(b) by 15 days.

(21) Appl. No.: 15/336,235

(22) Filed: Oct. 27, 2016

(65) Prior Publication Data

US 2017/0124426 A1 May 4, 2017

(30) Foreign Application Priority Data

Nov. 3, 2015 (CN) .......................... 2015 1 0736383
Feb. 23, 2016 (JP) ................................ 2016-032376

(51) Int. Cl.
*G06K 9/00* (2006.01)
*G06K 9/62* (2006.01)
*A61B 8/08* (2006.01)
*G06T 7/20* (2017.01)
*G06T 7/254* (2017.01)

(Continued)

(52) U.S. Cl.
CPC .......... *G06K 9/6215* (2013.01); *A61B 8/5223* (2013.01); *A61B 8/5246* (2013.01); *A61B 8/5253* (2013.01); *A61B 8/5276* (2013.01);

*G06K 9/00744* (2013.01); *G06T 7/20* (2013.01); *G06T 7/254* (2017.01); *A61B 8/469* (2013.01); *G01S 15/8995* (2013.01); *G06K 2009/3291* (2013.01); *G06K 2209/05* (2013.01);

(Continued)

(58) Field of Classification Search
CPC ............... G06K 9/6215; G06T 7/2033; G06T 2207/10132; G06T 2207/20104; A61B 8/5223; A61B 8/5238; A61B 8/5276
See application file for complete search history.

(56) References Cited

U.S. PATENT DOCUMENTS 4,689,986 A * 9/1987 Carson ................... A61B 8/481
600/438
5,219,401 A * 6/1993 Cathignol ........ A61B 17/22004
600/439

(Continued)

FOREIGN PATENT DOCUMENTS

JP 2008-289632 12/2008

*Primary Examiner* — Amir Alavi
(74) *Attorney, Agent, or Firm* — Oblon, McClelland, Maier & Neustadt, L.L.P.

(57) ABSTRACT

An ultrasound diagnosis apparatus according to an embodiment includes processing circuitry. The processing circuitry acquires a plurality of frames representing ultrasound images starting with an initial frame in time series. The processing circuitry compares a current frame and a previous frame to the current frame for determining the similarity therebetween, and generates a reference frame based on weighting processing on the initial frame and the previous frame using results of the comparison. The processing circuitry implements tracking processing between the reference frame and the current frame.

12 Claims, 8 Drawing Sheets

(51) Int. Cl.
*A61B 8/00* (2006.01)
*G01S 15/89* (2006.01)
*G06K 9/32* (2006.01)

(52) U.S. Cl.
CPC ............... *G06T 2207/10132* (2013.01); *G06T 2207/20104* (2013.01); *G06T 2207/30096* (2013.01)

(56) References Cited

U.S. PATENT DOCUMENTS

| | | | | |
|---|---|---|---|---|
| 5,233,994 | A * | 8/1993 | Shmulewitz | A61B 8/08 600/438 |
| 5,255,683 | A * | 10/1993 | Monaghan | A61B 8/06 600/458 |
| 6,340,348 | B1 * | 1/2002 | Krishnan | A61B 8/481 600/447 |
| 2011/0190629 | A1 * | 8/2011 | Guenther | A61B 8/08 600/437 |
| 2011/0237945 | A1 * | 9/2011 | Foroughi | A61B 8/4245 600/438 |
| 2013/0346050 | A1 * | 12/2013 | Kim | A61B 34/10 703/11 |
| 2017/0124426 | A1 * | 5/2017 | Li | G06K 9/6215 |
| 2017/0330331 | A1 * | 11/2017 | Bhatt | G06T 7/215 |

* cited by examiner

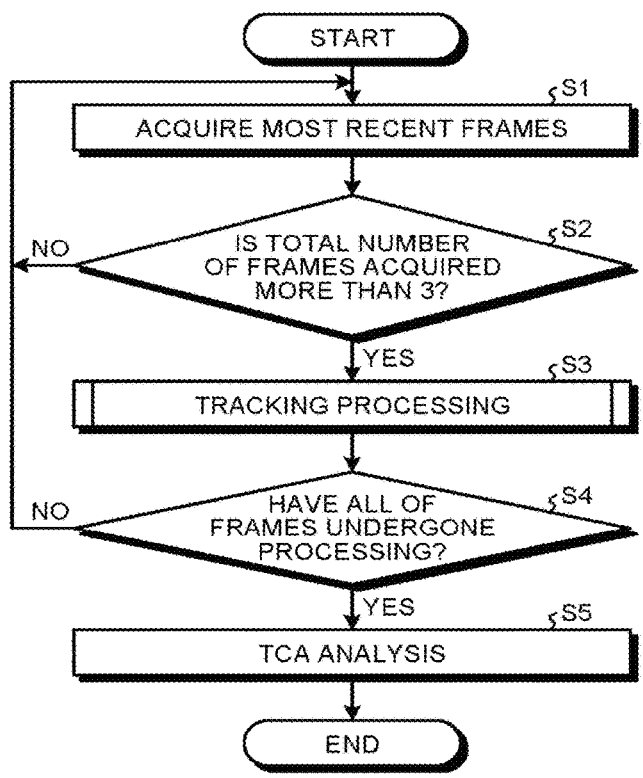

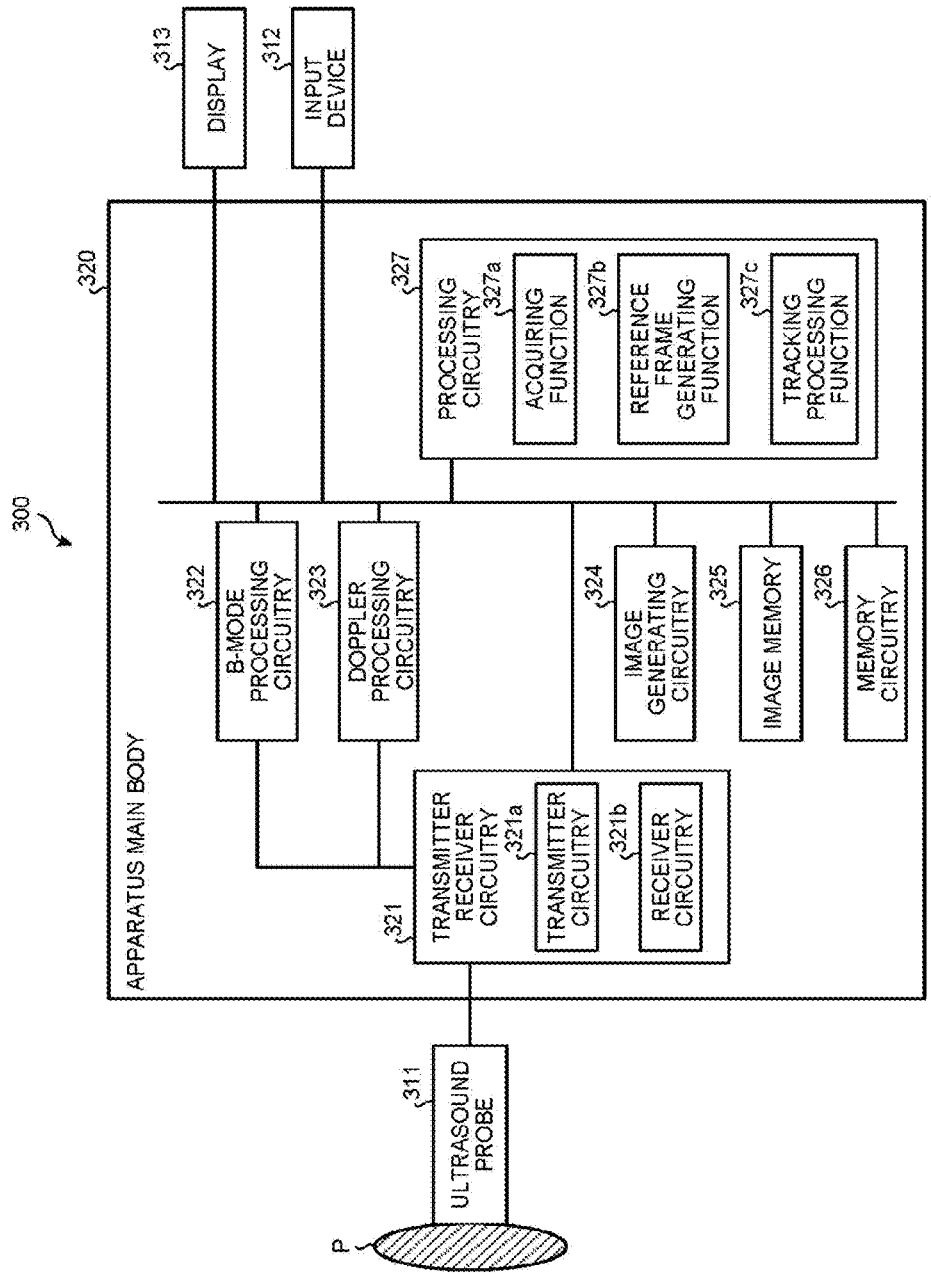

ULTRASOUND DIAGNOSIS APPARATUS, IMAGE PROCESSING APPARATUS AND IMAGE PROCESSING METHOD

CROSS-REFERENCE TO RELATED APPLICATIONS

This application is based upon and claims the benefit of priority from Chinese Patent Application No. 201510736383.3 filed on Nov. 3, 2015, and Japanese Patent Application No. 2016-032376, filed on Feb. 23, 2016; the entire contents of which are incorporated herein by reference.

FIELD

Embodiments described herein relate generally to an ultrasound diagnosis apparatus, an image processing apparatus and an image processing method for tracking medical images.

BACKGROUND

In clinical applications, TCA (time curve analysis) is an important measure for quantitative analysis of abnormal zone (tumor etc.) in an ultrasound image sequence. However, it is well known that in time curve analysis, the region of interest (ROI) which the observer is interested in, such as a tumor region, would vary continuously in a series of ultrasound images obtained over time, and motion tracking of ROI is one important step for obtaining reliable TCA results for the ROI (such as tumor region).

In order to enhance the precision of tracking ROI's motion, patent document 1 (Japanese Patent Application No. 2008-289623) proposed a solution in which image information (frames) before and after a specified time phase is read out from memory circuitry to obtain an intermediate imaginary frame and a small region image (ROI) is calculated. In this solution, the calculation on ROI's moving position adopts the image correlation processing such as region matching method. By means of this technical solution, ROI with low correlation may be determined as unwanted images such as noise, and luminance information of corresponding positions can be decreased.

However, the technical solution in patent document 1 did not take into account the occurrence of the inaccurate image information before and after a specified time phase. For example, in case that missing frame or periodical drastic variation of ultrasound image intensity occurs during sampling, the expected ROI may not exist in the two frames before and after the specified time phase. Even if a reference frame is obtained based on these two frames, the subsequent calculation result is not accurate and ROI motion tracking with high precision cannot be implemented, since there is no expected ROI in the reference frame. In addition, in patent document 1, the region matching method is used for the calculation of ROI's moving position. However, its region matching is implemented between only two regions obtained by the above mentioned method. In case that frame loss or large variation of image intensity occurs in the process, the differential value of moving positions is also inaccurate.

BRIEF DESCRIPTION OF THE DRAWINGS

FIG. 9 is a flow chart showing a flow of the entire processing by the medical image processing apparatus according to the first embodiment; and FIG. 10 is a module diagram showing an exemplary configuration of an ultrasound diagnosis apparatus according to a third embodiment.

DETAILED DESCRIPTION

Specific embodiments will be described in detail below with reference to accompanying drawings of the specification. The embodiments are only for illustration but not limited to the configuration shown in the embodiments. In the following embodiments, tracking a tumor region as a region of interest (ROI) is described as an example. However, the applications are not limited to tumor regions, and other ROIs may also be tracked.

An ultrasound diagnosis apparatus according to an embodiment includes processing circuitry. The processing circuitry acquires a plurality of frames representing ultrasound images starting with an initial frame in time series. The processing circuitry compares a current frame and a previous frame to the current frame for determining the similarity therebetween, and generates a reference frame based on weighting processing on the initial frame and the previous frame using results of the comparison. The processing circuitry implements tracking processing between the reference frame and the current frame.

First Embodiment

Figure 1:
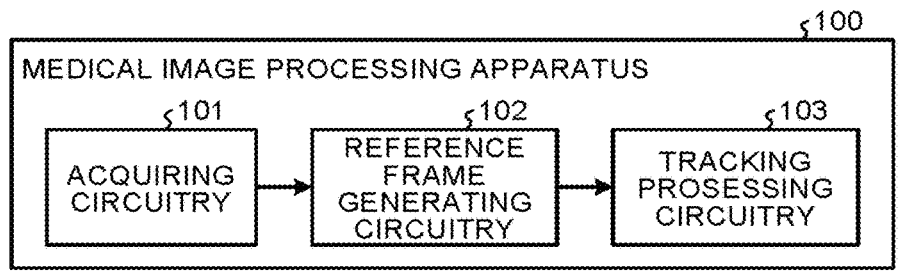
FIG. 1 is a module diagram showing a medical image processing apparatus according to a first embodiment.

FIG. 1 is a module diagram showing a medical image processing apparatus 100 according to the first embodiment.

As shown in FIG. 1, the medical image processing apparatus 100 includes acquiring circuitry 101, reference frame generating circuitry 102 and tracking processing circuitry 103. The acquiring circuitry 101 is referred to also as an acquiring unit; the reference frame generating circuitry 102, a reference frame generating unit; and the tracking processing circuitry 103, a tracking processing unit.

The medical image processing apparatus 100 thus configured acquires a plurality of frames, which are ultrasound images captured in time series by an ultrasound diagnosis apparatus, in order of times of the capturing.

Subsequently, the medical image processing apparatus 100 executes the following image processing method when tracking, for example, an ROI that is a tumor region. The image processing method by the medical image processing apparatus 100 will be described using FIG. 9. FIG. 9 is a flow chart showing a flow of the entire processing for the image processing method by the medical image processing apparatus 100 according to the first embodiment.

For example, as shown in FIG. 9, the medical image processing apparatus 100 acquires the most recent frames (step S1). For example, the medical image processing apparatus 100 acquires the most recent frames of ultrasound images captured in real time by an ultrasound diagnosis apparatus. The medical image processing apparatus 100 may acquire a plurality of ultrasound images captured by an ultrasound diagnosis apparatus and stored in a certain memory unit, in order of times of the capturing.

Next, the medical image processing apparatus 100 determines whether the total number of frames acquired is more than 3 (step S2). Here, if not determining that the total number of frames acquired is more than 3 (No at step S2), the medical image processing apparatus 100 proceeds to step S1 to acquire the most recent frames. On the other hand, if determining that the total number of frames acquired is more than 3 (Yes at step S2), the medical image processing apparatus 100 executes tracking processing (step S3). For example, every time acquiring the most recent frames, the medical image processing apparatus 100 generates a reference frame and executes tracking processing between the reference frame and each of the most recent frames. Details of the tracking processing will be described later. The "most recent frame" is referred to also as a "current frame".

After the tracking processing, the medical image processing apparatus 100 determines whether all of the frames have undergone the processing (step S4). Here, when not determining that all of the frames have undergone the processing (No at step S4), the medical image processing apparatus 100 proceeds to step S1 to acquire the most recent frames. On the other hand, when determining that all of the frames have undergone the processing (Yes at step S4), the medical image processing apparatus 100 executes TCA analysis (step S5). Details of the tracking processing by the units in the medical image processing apparatus 100 will be described herein below.

The acquiring circuitry 101 can be implemented with a processor to acquire a plurality of frames representing the ultrasound image starting with an initial frame (Frame$_1$) in time series. The ultrasound image is obtained by taking an examined subject as the inspection object. In the embodiments, the plurality of frames obtained in time series are denoted as: Frame$_1$ (initial frame), . . . , Frame$_{i-1}$ (previous frame of the current frame), Frame$_i$ (current frame), wherein i≥3. Each of the frames representing the ultrasound image which are obtained in time series is saved into memory circuitry (memory) corresponding to the medical image processing apparatus 100 after going through the tracking processing to be described below and being determined as successful tracking process.

The initial frame in the embodiments may either be a frame upon the beginning of capturing, or a frame after a period of capturing. However, the initial frame need to be a frame from which the operator can accurately select a ROI (tumor). The ROI in the embodiments refers to a target region the operator is interested in and wish to observe through a display apparatus (display) external to the medical image processing apparatus 100. As an approach of setting ROI, ROI can be marked by manual operation using an input unit corresponding to the medical image processing apparatus 100 after selecting the initial frame such that a ROI is set in the initial frame.

Figure 8:
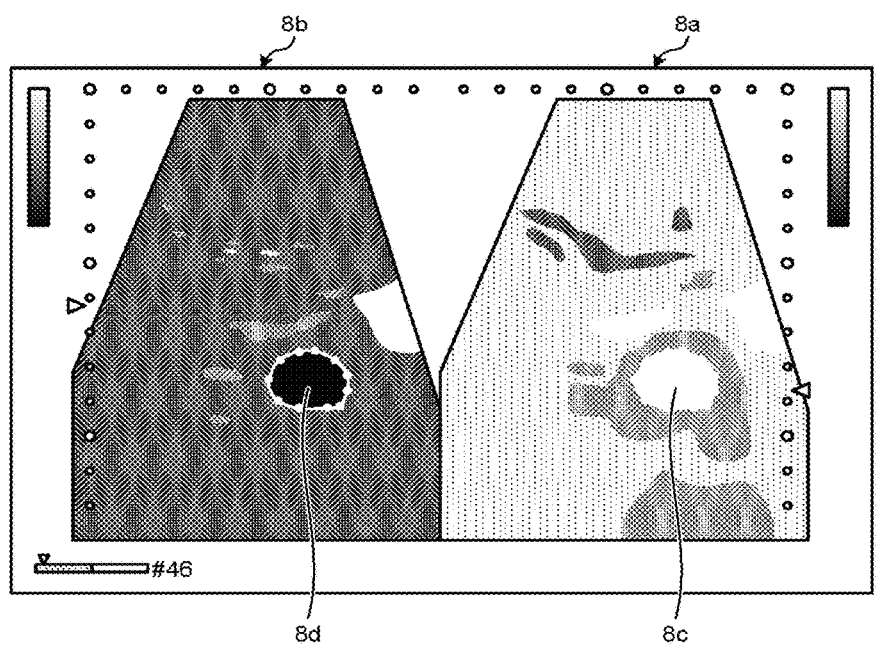
FIG. 8 is a diagram showing the ultrasound image and its ROI displayed on a display.

FIG. 8 is a diagram showing the ultrasound image and its ROI displayed on a display. The illustrations in the right-hand side in FIG. 8 and in the left-hand side in FIG. 8 are ultrasound images of an initial frame based on the same reflected wave data obtained by scanning an examined subject in the presence of a contrast agent. The illustration in the left-hand side in FIG. 8 shows an ultrasound image 8*b* visualizing only the contrast agent, and the illustration in the right-hand side in FIG. 8 an ultrasound image 8*a* of the B mode of the background in the illustration in the left-hand side in FIG. 8. The operator sets an ROI with reference to, for example, the ultrasound image 8*a* or the ultrasound image 8*b*. More specifically, the operator sets an ROI 8*c* in the ultrasound image 8*a*. Subsequently, the medical image processing apparatus 100 sets, in conjunction with the setting of the ROI 8*c*, an ROI 8*d* on the ultrasound image 8*b* at a position corresponding to the ROI 8*c*. The operator may set the ROI 8*d* in the ultrasound image 8*b*. In this case, the medical image processing apparatus 100 sets, in conjunction with the setting of the ROI 8*d*, the ROI 8*c* on the ultrasound image 8*a* at a position corresponding to the ROI 8*d*. The initial frame is thus the frame set with an ROI.

The reference frame generating circuitry 102 may be implemented with a processor, and compares the current frame and a previous frame to the current frame for determining the similarity therebetween and generates a reference frame based on weighting processing on the previous frame and the initial frame using results of the comparison. For example, the reference frame generating circuitry 102 compares the similarity between the captured current frame (Frame$_i$) and its previous frame (Frame$_{i-1}$) and assigns weights to the initial frame and the previous frame from the similarity. More specifically, the reference frame generating circuitry 102 increases the weight for the previous frame (Frame$_{i-1}$) if the similarity is high or increases the weight for the initial frame (Frame$_1$) if the similarity is low, thus generating a reference frame (Frame$_r$) using the weighted previous frame and initial frame. In the generation of reference frame, the initial frame (Frame$_1$) set with an ROI is used. Therefore, an ROI is also set in the generated reference frame similarly, and the ROI can be observed from the display during observation of a tumor. In the present embodiment, the ROI 8*c* and the ROI 8*d* are set in the ultrasound images, for example, as described using FIG. 8. Details on the generation of reference frame will be set forth below.

The tracking processing circuitry 103 may be implemented with a processor and carries out tracking processing between the reference frame and the current frame and between the current frame and the previous frame. For example, the tracking processing circuitry 103 carries out tracking processing among frames so as to determine whether or not to save the current frame. The tracking processing includes: a matching processing of matching an ROI of one frame for a matched region of another, and a comparing and determining processing for comparing a variation amount between the ROI of one frame and the matched region of another with a predetermined threshold.

Methods for matching processing for matching two frames and comparing variation amount after matching with threshold are disclosed in prior art. The tracking processing circuitry 103 in the present embodiment may carry out the matching processing only between the reference frame and the current frame with prior art methods and compare the variation amount between the matched frames against a threshold to determine whether or not to save the current frame. However, in case that matching is implemented between only two frames and then the variation amount is compared against the threshold, if the reference frame is inaccurate, the subsequent processing results may be inaccurate as well. Therefore it is impossible to accurately determine whether the current frame is reliable.

In contrast to this, preferably, the tracking processing circuitry 103 of the present embodiment carries out matching and threshold-comparison among three frames (between the reference frame (Frame$_r$) and the current frame (Frame$_i$), and between the current frame (Frame$_i$) and the previous frame (Frame$_{i-1}$)). It is possible to determine whether or not to save the current frame more accurately by carrying out matching and threshold-comparison between the current frame (Frame$_i$) and previous frame (Frame$_{i-1}$) too.

[Generation of Reference Frame]

The generation of reference frame by the reference frame generating circuitry 102 will be described in detail below.

The reference frame generating circuitry 102 implements the similarity comparison to increase the weight for the previous frame if the similarity is high and increase the weight for the initial frame if the similarity is low, and adds the initial frame and the previous frame, which are subjected to weighting processing, thereby generating the reference frame.

For example, during the generation of reference frame, the reference frame generating circuitry 102 first displaces the ROI in the previous frame with respect to the ROI in initial frame, and then assigns weights to the initial frame and the displaced previous frame to generate a reference frame. The displacement and weighting will be described in detail below.

The following mathematical expression 1 is utilized for the generation of reference frame.

$$\text{Frame}_r = a \times \text{Frame}_1 + b \times T(\text{Frame}_{i-1}) \text{ where } a,b \in [0,1] \quad \text{Expression 1}$$

In the above mathematical expression 1, Frame$_1$ denotes the initial frame, Frame$_{i-1}$ denotes the previous frame of the current frame, T(Frame$_{i-1}$) denotes the displacement of position of ROI in the previous frame with respect to the position of ROI in the initial frame, a and b denote weight coefficients for the initial frame (Frame$_1$) and the previous frame (Frame$_{i-1}$) respectively, which will be referred to as the weight a for initial frame and the weight b for previous frame respectively, and Frame$_r$ denotes the generated reference frame which is obtained by adding the initial frame assigned with weight a and the previous frame displaced with respect to the initial frame and assigned with weight b. That is, the reference frame generating circuitry 102 displaces the ROI in the previous frame with respect to the ROI in the initial frame before the adding.

Figure 2:
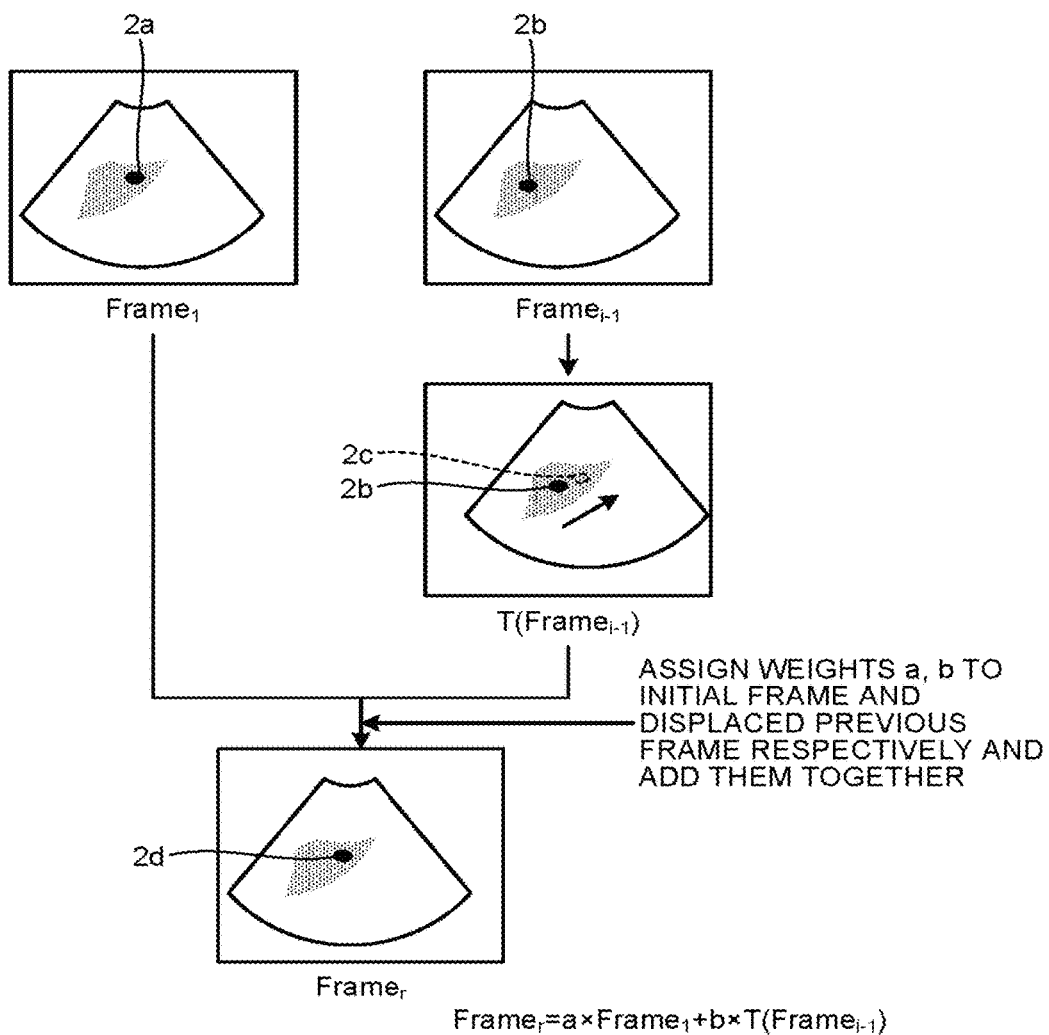
FIG. 2 is a diagram showing the process of displacing an ROI in a previous frame with respect to the ROI in an initial frame during generating a reference frame.

Subsequently, the displacement of T(Frame$_{i-1}$) (namely displacement of ROI in previous frame with respect to ROI in initial frame) in the mathematical expression 1 will be explained with reference to FIG. 2. Frame$_1$ in FIG. 2 denotes the initial frame read out from the memory circuitry, and Frame$_{i-1}$ denotes the previous frame read out from the memory circuitry. T(Frame$_{i-1}$) denotes the image after the ROI in previous frame is displaced with respect to the ROI in initial frame, and Frame$_r$ denotes the generated reference frame. For example, as shown in FIG. 2, an ROI 2a is set in the initial frame (Frame$_1$) and an ROI 2b in the previous frame (Frame$_{i-1}$).

Since the acquisition process of ultrasound image is a dynamic processes, positions of ROIs in a plurality of frames obtained by the acquiring circuitry 101 in time series might not be consistent completely. In order to add positions of ROIs in two frames (the initial frame and the previous frame), it is need to displace the position of ROI in one frame with respect to that of the other. In the present embodiment, because the initial frame functions as the reference frame to determine that the ROI exists, upon the displacement, the position of ROI in the previous frame is displaced with respect to the position of ROI in the initial frame. More specifically, the reference frame generating circuitry 102 displaces the ROI 2b in the previous frame (Frame$_{i-1}$) with respect to the ROI 2a in the initial frame (Frame$_1$). That is, the reference frame generating circuitry 102 displaces the ROI 2b in the previous frame (Frame$_{i-1}$) to a desired target position 2C in T(Frame$_{i-1}$). In the example shown in FIG. 2, an ROI 2d is set in the reference frame. The position of the ROI 2d is set in the reference frame corresponds to the position of the ROI 2a in the initial frame.

In addition, in the generation of reference frame, weights a and b assigned to the initial frame and the previous frame respectively satisfy the relationship in the following mathematical expression 2, that is to say, if weight b is small, weight a is large, and if weight b is large, weight a is small.

$$a = 1 - b \quad \text{Expression 2}$$

In addition, weight b in mathematical expression 2 is determined by the similarity between the current frame and the previous frame and satisfies the following mathematical expression 3.

$$b = 0.5 \times CC(i-1, i) \quad \text{Expression 3}$$

In mathematical expression 3, CC(i−1, i) denotes the similarity between the current frame (Frame$_i$) and the previous frame (Frame$_{i-1}$), which may be calculated using the calculation method in prior art. Since CC(i−1, i) is calculated based on the current frame (Frame$_i$) and the previous frame (Frame$_{i-1}$), while weight b has a relationship with CC(i−1, i) as shown in mathematical expression 3, weight b is a parameter that establishes a correspondence with the current frame (Frame$_i$) and previous frame (Frame$_{i-1}$).

Thus, based on the relationship between weights a, b and similarity CC(i−1, i) in the mathematical expression 2 and mathematical expression 3, when the current frame and the previous frame have high similarity, the previous frame in mathematical expression 1 is assigned with a larger weight, the initial frame with a smaller weight, and when the current frame and previous frame have a low similarity, the previous frame in mathematical expression 1 is assigned with a smaller weight and the initial frame with a larger weight.

[Effect of Generating Reference Frame]

The reference frame in the present embodiment is generated based on the initial frame, the previous frame and the current frame, wherein the initial frame is the frame comprising ROI. By generating the reference frame with three frames including the initial frame, it is possible to ensure the desired ROI exists in the reference frame, and exclude error detection due to large variation of luminance of ultrasound image or frame loss.

In addition, in the generation of reference frame in the present embodiment, different weights are adaptively assigned to the initial frame and the previous frame according to the similarity between the previous frame and the current frame, wherein if the previous frame and the current frame have high similarity, the weight for previous frame is increased, and if the previous frame and the current frame have low similarity, the weight for the initial frame is increased, thereby generating the reference frame. By means of this method, for a high similarity, the weight for the previous frame similar to the current frame is increased, and for a low similarity, it is determined that detection failure of ROI might occur and the weight for the initial frame comprising ROI is increased, thereby guaranteeing the desired ROI exists in the reference frame, which can exclude error detection due to large variation of luminance of ultrasound image or frame loss.

Figure 3:
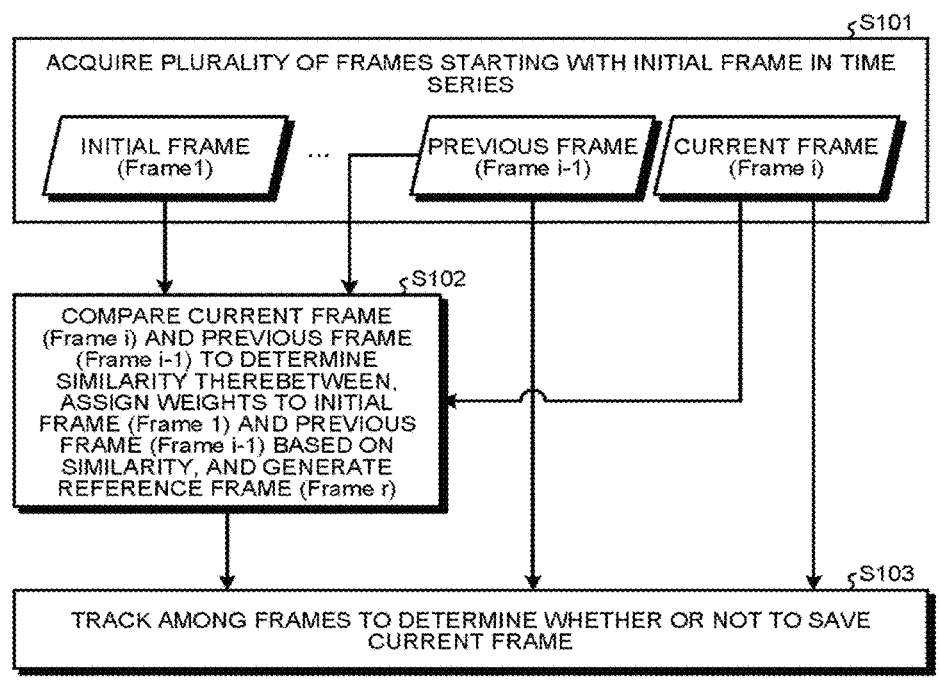
FIG. 3 is a flow chart showing the procedure of tracking processing by the medical image processing apparatus according to the first embodiment.

The procedure of the tracking processing by the medical image processing apparatus 100 according to the first embodiment will be described below with reference to FIG. 3. FIG. 3 is a flow chart showing the procedure of the tracking processing by the medical image processing apparatus 100 according to the first embodiment.

The acquiring circuitry 101 of the medical image processing apparatus 100 acquires a plurality of frames representing the ultrasound image starting with the initial frame (Frame$_1$) in time series (step S101). The initial frame includes the site that the observer is interested in, namely the ROI.

In step S102, the reference frame generating circuitry 102 displaces ROI in the previous frame (Frame$_{i-1}$) with respect to the ROI in initial frame (Frame$_1$) and compare the current frame (Frame$_i$) and the previous frame (Frame$_{i-1}$) to determine the similarity therebetween. Weights are assigned to the initial frame (Frame$_1$) and the previous frame (Frame$_{i-1}$) based on the similarity between the current frame (Frame$_i$) and the previous frame (Frame$_{i-1}$). If the similarity is high, the weight for the previous frame is increased, and if the similarity is low, the weight for the initial frame is increased, and the previous frame and initial frame assigned with weight respectively are added together to generate the reference frame (Frame$_r$). The similarity comparison is implemented in the entire region of the current frame of ultrasound image and the previous frame of ultrasound image.

Next, the tracking processing circuitry 103 implements tracking processing among frames to determine whether the current frame is acceptable. If so, the current frame is stored, and if not, the current frame is discarded (step S103).

The tracking processing includes: a matching processing for matching a ROI of one frame for the matched region of another, and a comparing and determining processing for comparing a variation amount between the ROI of one frame and the matched region of another against a predetermined threshold.

Methods for matching processing for matching between two frames and comparing variation amount after matching against threshold are disclosed in prior art. In step S103, it is possible to utilize prior art method to implement the matching processing between only the reference frame and the current frame and compare the variation amount between frames after matching with the threshold to determine whether or not to save the current frame. However, in case that matching is implemented between only two frames and then variation amount is compared against the threshold, if the reference frame is inaccurate, it is possible that subsequent processing results are inaccurate too. Therefore it is impossible to accurately determine whether the current frame is saved.

In contrast to this, preferably, in step S103 in the first embodiment, the tracking processing circuitry 103 carries out ROI matching among three frames (between the reference frame (Frame$_r$) and the current frame (Frame$_i$), and between the current frame (Frame$_i$) and the previous frame (Frame$_{i-1}$)). Subsequently, the tracking processing circuitry 103 calculates a first variation amount between a region in the current frame matched with the reference frame and a region in the reference frame corresponding to the matched region. In addition, the tracking processing circuitry 103 calculates a second variation amount between a region in the current frame matched with the previous frame and a region in the previous frame corresponding to the matched region. The tracking processing circuitry 103 then determines, when the calculated first variation amount and second variation amount are both smaller than a threshold, that the tracking is successful, and, when at least one of the first variation amount and second variation amount is greater than or equal to the threshold, that the tracking is unsuccessful.

Figure 7:
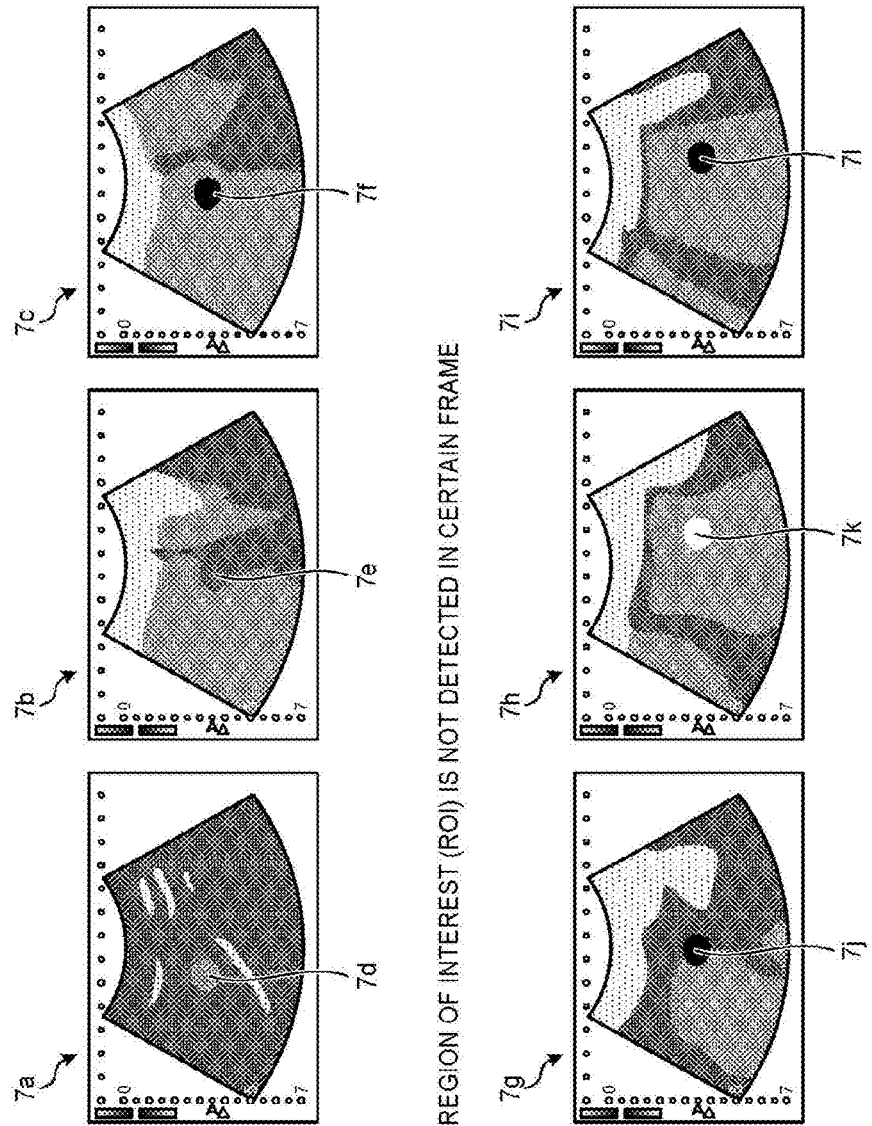
FIG. 7 is a diagram schematically showing frame loss due to large variation of ultrasound image luminance and probe motion etc.

FIG. 7 is a diagram schematically showing frame loss due to large variation of ultrasound image luminance and probe motion etc in the prior art. The upper part of FIG. 7 is used for explaining frame loss due to large variation of ultrasound image luminance, and the lower part of FIG. 7 for explaining frame loss due to probe motion, body motion of an examined subject.

The upper part of FIG. 7 shows an ultrasound image 7a, an ultrasound image 7b and an ultrasound image 7c. The ultrasound images shown in the upper part of FIG. 7 are assumed to be acquired in time series starting from the ultrasound image 7a, followed by the ultrasound image 7b and then the ultrasound image 7c. In addition, in the example shown in the upper part of FIG. 7, the ultrasound image 7a is taken as an initial frame, and an ROI 7d is set in the ultrasound image 7a taken as the initial frame.

Here, in TCA analysis, changes in concentration of the contrast agent in an ROI over time are observed after a contrast agent is taken into the ROI and until the contrast agent is discharged from the ROI, for example. When the contrast agent is taken into an ROI, a sharp change occurs in luminance of an ultrasound image. For example, the ultrasound images 7b and 7c show sharper changes in luminance that the ultrasound image 7a. In such a case, conventional medical image processing apparatus are possibly unable to accurately track an ROI, for example, through pattern matching between adjacent two frames. More specifically, conventional medical image processing apparatus is incapable of tracking an ROI 7e in the ultrasound image 7b through pattern matching with the ultrasound image 7a. Conventional medical image processing apparatus is also incapable of tracking an ROI 7f in the ultrasound image 7c through pattern matching with the ultrasound image 7b in which tracking the ROI is impossible. The ultrasound image 7b and the ultrasound image 7c are treated as unwanted frames in TCA analysis when accurately tracking the ROIs therein is impossible with conventional medical image processing apparatus.

The lower part of FIG. 7 shows an ultrasound image 7g, an ultrasound image 7h and an ultrasound image 7i. The ultrasound images shown in the lower part of FIG. 7 are assumed to be acquired in time series starting from the ultrasound image 7g, followed by the ultrasound image 7h and then the ultrasound image 7i. In addition, in the example shown in the lower part of FIG. 7, the ultrasound image 7g is taken as an initial frame, and an ROI 7j is set in the ultrasound image 7g taken as an initial frame.

Here, a captured range may move in response to the movement of a probe or body motion of an examined subject. For example, the captured ranges of the ultrasound image 7h and the ultrasound image 7i are moved, compared with the captured range of the ultrasound image 7g. In such a case, conventional medical image processing apparatus is possibly unable to accurately track an ROI, for example, through pattern matching between adjacent two frames. More specifically, conventional medical image processing apparatus is incapable of tracking an ROI 7k in the ultrasound image 7h through pattern matching with the ultrasound image 7g. Conventional medical image processing apparatus is also incapable of tracking an ROI 7l in the ultrasound image 7i through pattern matching with the ultrasound image 7h in which tracking the ROI is impossible. The ultrasound image 7h and the ultrasound image 7i are treated as unwanted frames in TCA analysis when accurately tracking the ROIs therein is impossible with conventional medical image processing apparatus.

However, the image processing method described above enables discarding unwanted frames as those shown in FIG. 7, that is, enables excluding worthless images generated due to, for example, large variation of luminance of ultrasound image and probe motion. More specifically, the medical image processing apparatus 100 discards the ultrasound image 7b shown in the upper part of FIG. 7. Furthermore, the medical image processing apparatus 100 is enabled to accurately track the ROI in the ultrasound image 7c shown in the upper part of FIG. 7 through matching with the reference frame and through matching with the ultrasound image 7b taken as the previous frame. The medical image processing apparatus 100 can thus retain the ultrasound image 7c. In addition, the medical image processing apparatus 100 discards the ultrasound image 7h shown in the lower part of FIG. 7. Furthermore, the medical image processing apparatus 100 is enabled to accurately track the ROI in the ultrasound image 7i shown in the lower part of FIG. 7 through matching with the reference frame and through matching with the ultrasound image 7h taken as the previous frame. The medical image processing apparatus 100 can thus retain the ultrasound image 7i.

Modification of the First Embodiment

In the embodiments, description is set forth under the assumption that weights a, b satisfy the relationship of mathematical expression 2 and weight b and CC(i−1, i) satisfy the relationship of mathematical expression 3. However, it is also possible to assume that weight a becomes a fixed value greater than zero and does not vary with weight b, and weight b and similarity CC(i−1, i) satisfy another positive correlation relationship.

The relationships among weights a, b and CC(i−1, i) are not specifically limited, as long as a large weight is assigned to the previous frame for a high similarity between the current frame and the previous frame, and a small weight is assigned to the previous frame for a low similarity between the current frame and the previous frame.

Second Embodiment

Figure 4:
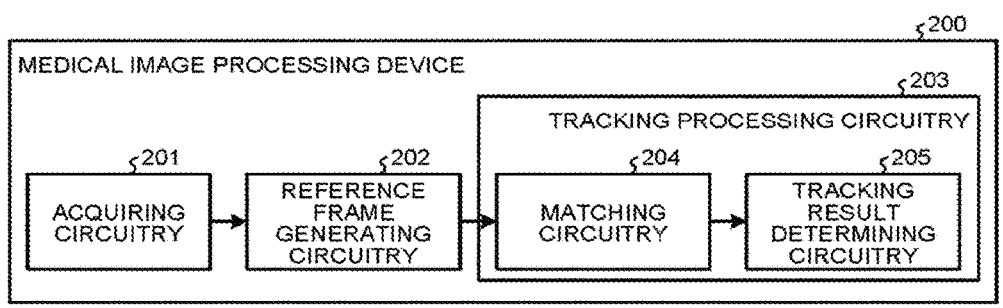
FIG. 4 is a module diagram showing the medical image processing apparatus according to a second embodiment.

The second embodiment is a variant of the first embodiment. As shown in FIG. 4, a medical image processing apparatus 200 of the second embodiment comprises: acquiring circuitry 201 and reference frame generating circuitry 202 identical to the acquiring circuitry 101 and the reference frame generating circuitry 102 of medical image processing apparatus 100 of the first embodiment; and tracking processing circuitry 203 different from the tracking processing circuitry 103 of the first embodiment.

The tracking processing circuitry 203 of the second embodiment comprises a matching circuitry 204 and tracking result determining circuitry 205.

Figure 5:
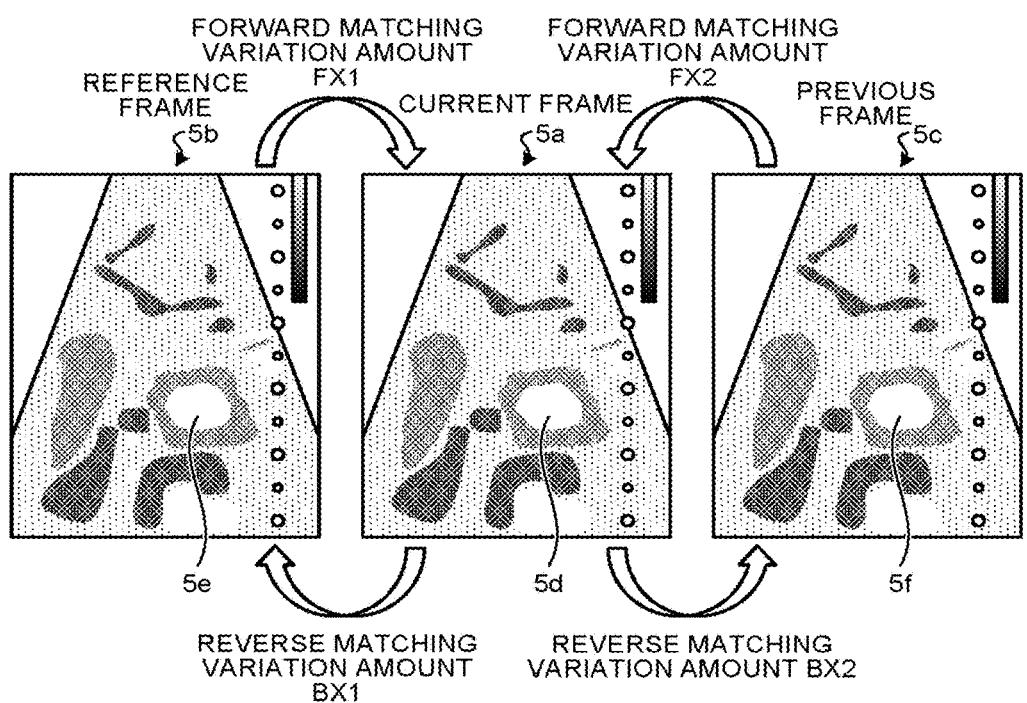
FIG. 5 is a schematic diagram illustrating forward matching and reverse matching by a matching unit and tracking processing by a tracking result determining unit.

FIG. 5 is a schematic diagram for illustrating the forward matching and reverse matching by the matching circuitry 204 and the tracking processing by the tracking result determining circuitry 205.

The middle illustration in FIG. 5 shows an ultrasound image 5a taken as the current frame. The left illustration in FIG. 5 shows an ultrasound image 5b taken as the reference frame, and the right illustration in FIG. 5 an ultrasound image 5c taken as the previous frame. The left illustration in FIG. 5 also shows an ROI 5e set in the ultrasound image 5b taken as the reference frame, and the right illustration in FIG. 5 shows an ROI 5f set in the ultrasound image 5c taken as the previous frame.

As shown in FIG. 5, the matching circuitry 204 in the present embodiment implements forward matching and reverse matching both in matching between the reference frame and the current frame and in matching between the current frame and the previous frame. The forward matching refers to matching from any one of the reference frame and the previous frame as other frames to the current frame, while the reverse matching refers to matching from the current frame to other frames (reference frame, previous frame). Since the reference frame is better than the previous frame in terms of reliability of ROI, preferably, the matched region (Block$_i$) of the current frame is obtained based on the ROI (Block$_r$) of the reference frame.

Reverse matching is a matching implemented after the forward matching is implemented and a matched region (Block$_i$) of the current frame is obtained, which further obtains a new matched region (Block$_r$', Block$_{i-1}$') in the reference frame and the previous frame based on the matched region (Block$_i$) in the current frame.

The input (input information) to the matching circuitry 204 and the output (output information) from the matching circuitry 204 upon the forward matching and reverse matching among different frames are shown as follows.

In case of implementing forward matching from the reference frame to the current frame, the matching circuitry 204 generates the matched region (Block$_i$) in the current frame with the reference frame and current frame representing the entire region of ultrasound image and the ROI (Block$_r$) in the reference frame. More specifically, the matching circuitry 204 searches the current frame for a region similar to the ROI set in the reference frame by using, for example, pattern matching. In the example shown in FIG. 5, the matching circuitry 204 sets a matched region 5d in the ultrasound image 5a taken as the current frame shown in the middle illustration in FIG. 5.

In case of implementing reverse matching from the current frame to the reference frame, the matching circuitry 204 generates a new matched region (Block$_r$') in the reference frame with the reference frame and current frame representing the entire region of ultrasound image and the matched region (Block$_i$) in the current frame. More specifically, for example, the matching circuitry 204 searches the reference frame for a region similar to the matched region in the current frame that is set as a result of forward matching. The matching circuitry 204 then sets the region found by the searching in the reference frame as a new matched region.

In case of implementing forward tracking from the previous frame to the current frame, the matching circuitry 204 generates the matched region (Block$_i$) in the current frame with the current frame and the previous frame representing the entire region of ultrasound image and the ROI (Block$_{i-1}$) in the previous frame. However, as stated above, it is preferable in the present embodiment to generate the matched region (Block$_i$) in the current frame with the ROI in the reference frame. Therefore, in case that the matched region (Block$_i$) in the current frame has already obtained, preferably, the forward matching from the previous frame to the current frame is omitted, which may enhance the operation efficiency. Note that the ROI in the previous frame is a region set as a matched region with reference to a frame taken as a reference frame when this previous frame has been taken as a current frame.

In case of implementing reverse tracking from the current frame to the previous frame, the matching circuitry 204 generates a new matched region (Block$_{i-1}$) in the previous frame with the current frame and the previous frame representing the entire region of ultrasound image and the matched region (Block$_i$) in the current frame. More specifically, for example, the matching circuitry 204 searches the previous frame for a region similar to the matched region in the current frame. The matching circuitry 204 then sets the region found by the searching in the previous frame as a new matched region.

Subsequently, tracking result determining circuitry 205 calculates a first variation amount between a region in the current frame matched with the reference frame and a region in the reference frame corresponding to the matched region. For example, the tracking result determining circuitry 205 calculates, as the first variation amount, a differential between a region variation amount from the reference frame to the current frame and a region variation amount from the current frame to the reference frame. Here, when implementing forward matching between the reference frame and the current frame, the tracking result determining circuitry 205 sets the ROI in the reference frame before the matching as the corresponding region. When implementing reverse matching between the reference frame and the current frame, the tracking result determining circuitry 205 sets the ROI in the reference frame after the reverse matching thereto from the current frame as the corresponding region.

In addition, the tracking result determining circuitry 205 calculates a second variation amount between a region in the current frame matched with the previous frame and a region in the previous frame corresponding to the matched region. For example, the tracking result determining circuitry 205 calculates, as the second variation amount, a differential between a region variation amount from the reference frame to the current frame and a region variation amount from the current frame to the reference frame. Here, when implementing forward matching between the current frame and the previous frame, the tracking result determining circuitry 205 sets the ROI in the previous frame before the matching as the corresponding region. When implementing reverse matching between the current frame and the previous frame, the tracking result determining circuitry 205 sets the ROI in the previous frame after the reverse matching thereto from the current frame as the corresponding region.

More specifically, the tracking result determining circuitry 205 calculates the variation amount (FX1, FX2) between the matched region (Block$_i$) in the current frame and the ROI (Block$_r$) in the reference frame and the ROI (Block$_{i-1}$) in the previous frame read out from the memory, and the variation amount (BX1, BX2) between the matched region (Block$_i$) in the current frame and the new matched region (Block$_r$') in the reference frame and the new matched region (Block$_{i-1}$') in the previous frame respectively based on the matched region (Block$_i$) in the current frame obtained by the forward matching. Here, the variation amount FX1 is, for example, a displacement vector from the ROI (Block$_r$) in the reference frame to the matched region (Block$_i$) in the current frame, and the variation amount FX2 is, for example, a displacement vector from the ROI (Block$_{i-1}$) in the previous frame to the matched region (Block$_i$) in the current frame. The variation amount BX1 is a displacement vector from the matched region (Block$_i$) in the current frame to the new matched region (Block$_r$') in the reference frame, and the variation amount BX2 is displacement vector from the matched region (Block$_i$) in the current frame to the new matched region (Block$_{i-1}$') in the previous frame. The tracking result determining circuitry 205 then determines, when the calculated first variation amount and second variation amount are both smaller than a threshold, that the tracking is successful, and, when at least one of the first variation amount and second variation amount is greater than or equal to the threshold, that the tracking fails. That is, the tracking result determining circuitry 205 determines whether ||FX1|−|BX1|| and ||FX2|−|BX2|| are both smaller than the threshold. Here, the tracking result determining circuitry 205 determines tracking to be successful when both of them are smaller than a defined threshold, and determines tracking to be unsuccessful when they are not both smaller than the defined threshold. Optionally, the tracking processing circuitry 203 may include rejection processing circuitry configured to discard the current frame when the tracking result determining circuitry 205 determines tracking to be unsuccessful, and retain the current frame when the tracking result determining circuitry 205 determines tracking to be successful.

Figure 6:
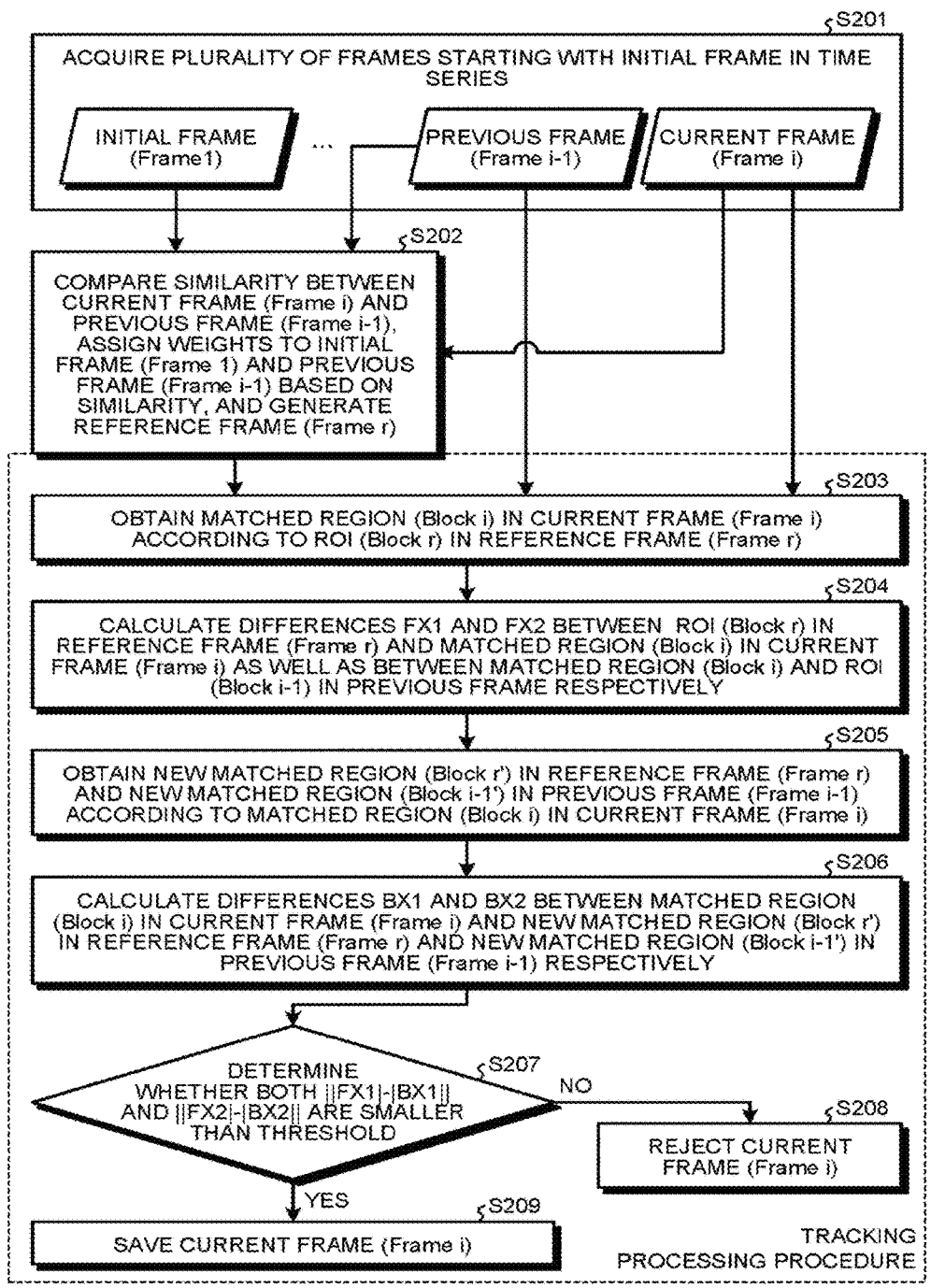
FIG. 6 is a flow chart showing the procedure of tracking processing by the medical image processing apparatus according to the second embodiment.

FIG. 6 is a flow chart showing the procedure of the tracking processing by the medical image processing apparatus 200 according to the second embodiment.

The acquiring circuitry 201 of the medical image processing apparatus 200 in the present embodiment acquires a plurality of frames representing ultrasound image starting with an initial frame (Frame$_1$) (step S201). The initial frame includes the site that the observer is interested in, namely the ROI.

In step S202, the reference frame generating circuitry 202 compares the current frame (Frame$_i$) and the previous frame (Frame$_{i-1}$) to determine the similarity therebetween. Weights are assigned to the initial frame (Frame$_1$) and the previous frame (Frame$_{i-1}$) based on the similarity between the current frame (Frame$_i$) and the previous frame (Frame$_{i-1}$). If the similarity is high, the weight for the previous frame is increased, and if the similarity is low, the weight for the initial frame is increased, and the previous frame and initial frame assigned with weight respectively are added together to generate the reference frame (Frame$_r$). The similarity-comparison is implemented in the entire region of the current frame of ultrasound image and the previous frame of ultrasound image.

The above steps S201 and S202 are identical to steps S101 and S102 in the first embodiment.

The tracking processing procedure in the second embodiment further includes steps S203 to S209.

In step S203, the matching circuitry 204 implements forward matching from the reference frame (Frame$_r$) to the current frame (Frame$_1$) first. That is, the matched region (Block$_i$) in the current frame (Frame$_i$) is obtained according to the ROI (Block$_r$) in the reference frame (Frame$_r$).

Next, in step S204, the tracking result determining circuitry 205 calculates differentials FX1 and FX2 between ROI (Block$_r$) in the reference frame (Frame$_r$) and the matched region (Block$_i$) in the current frame (Frame$_i$) and between the matched region (Block$_i$) in the current frame (Frame$_i$) and the ROI (Block$_{i-1}$) in the previous frame (Frame$_{i-1}$) respectively.

Next, in step S205, the matching circuitry 204 obtains a new matched region (Block$_r$') in the reference frame (Frame$_r$) and a new matched region (Block$_{i-1}$') in the previous frame (Frame$_{i-1}$) according to the matched region (Block$_i$) in the current frame (Frame$_i$).

Next, in step S206, the tracking result determining circuitry 205 calculates differentials BX1 and BX2 between the matched region (Block$_i$) in the current frame (Frame$_i$) and the new matched region (Block$_r$') in the reference frame (Frame$_r$), as well as the new matched region (Block$_{i-1}$') in the previous frame (Frame$_{i-1}$) respectively.

In the present embodiment, steps S203, S204, S205 and S206 are carried out in the described order. However, it is also possible to carry out differential calculation steps S204 and S206 based on the tracking result determining circuitry 205 after carrying out matching steps S203 and S205 by the matching circuitry 204.

Next, in step S207, based on the calculated above variation amounts (FX1, FX2, BX1, BX2), the tracking result determining circuitry 205 determines whether the difference between variation amounts (FX1, BX1) obtained by forward matching and reverse matching between reference frame and current frame is less than a predefined threshold, and determines whether the difference between two variation amounts between the current frame and the previous frame (one (FX2) is obtained by subtracting the matched region in the current frame from the ROI in the previous frame, the other (BX2) is obtained by implementing reverse matching from the current frame to the previous frame) is less than a predefined threshold. In other words, in step S207, it is determined whether $\|FX1|-|BX1\|$ and $\|FX2|-|BX2\|$ are both less than a threshold. When the variation amount is less than the threshold, it is determined that the tracking is successful and the current frame is saved (step S209), and when the variation amount is greater than or equal to the threshold, it is determined that the tracking fails and the current frame is discarded (step S208).

As a comparative example, it is supposed below that only a pair of tracking results are considered, that is, it is only determined whether $\|FX1|-|BX1\|<$threshold or $\|FX2|-|BX2\|<$threshold is satisfied. In case only the first pair of variation amounts (FX1, BX1) is considered, if the reference frame obtained by weighting is not very accurate, it is not possible to accurately determine whether the tracking of current frame is successful based on the first pair of variation amount (FX1, BX1), and in case only the second pair of variation amounts (FX2, BX2) is considered, if the tracking result for the previous frame saved in the memory circuitry slightly deviates, the deviation will be passed to the tracking determination of the current frame and be amplified. In extreme cases, if the ROIs disappear in both the previous frame and the current frame while images of both happen to have the same structural features, convergence of variation amount will also occur ($\|FX2|-|BX2\|$ is about 0), however the tracking of the current frame is in fact not successful now.

In contrast to this, the medical image processing apparatus 200 in the present embodiment determines the tracking is successful only when both of $\|FX1|-|BX1\|$ and $\|FX2|-|BX2\|$ are smaller than the threshold, and otherwise determines the tracking fails. With this determination method, it is possible to further enhance the detection precision relative to only determining $\|FX1|-|BX1\|$ or $\|FX2|-|BX2\|$.

With the processing procedure, it is possible to discard unwanted current frames when frame loss occurs due to large variation of luminance of ultrasound image or probe motion as shown in FIG. 7 described above, that is, it is possible to exclude worthless images generated due to large variation of luminance of ultrasound image and probe motion.

Modification of the Second Embodiment

In the second embodiment, the matched region (Block$_i$) in the current frame is generated with the ROI (Block$_r$) in the reference frame and the variation amount FX2 is directly calculated, omitting the matching of the ROI (Block$_{i-1}$) in the previous frame to the matched region (Block$_i$) in the current frame. However, the embodiments are not limited to this. It is possible to obtain the matched region (Block$_i$) based on the ROI (Block$_{i-1}$) of the previous frame and calculate the variation amount FX1 directly, omitting the matching of ROI (Block$_r$) in the reference frame to the matched region (Block$_i$) in the current frame. Furthermore, it is also possible to generate matched regions (Block$_i$) in two current frames with the ROI (Block$_r$) in the reference frame and the ROI (Block$_{i-1}$) in the previous frame, and implement respective tracking processing by implementing reverse matching respectively according to the matched regions (Block$_i$) in the two current frames. In case that variation amounts obtained based on the obtained two matched regions (Block$_i$) satisfy the relationship with threshold, it is determined that the tracking is successful, otherwise it is determined that the tracking fails.

The variant is identical to the second embodiment except for the criteria for generating matched region (Block$_i$) in the current frame.

With the medical image processing apparatus according to the above first and second embodiments and their variants, by generating reference frame with the current frame, the previous frame of current frame and the initial frame set with an ROI and tracking ROI among the generated reference frame, the current frame and the previous frame of the current frame, it is possible to discard unwanted current frames, and exclude worthless images (noise, etc.) generated due to large variation of luminance of ultrasound image and probe motion.

In the medical image processing apparatus according to the first embodiment and the second embodiment, processing functions that may be implemented by the acquiring circuitry, the reference frame generating circuitry and the tracking processing circuitry as constituent elements are saved into the memory circuitry in form of computer executable programs. The processing circuitry is a processor for reading and executing programs from the memory circuitry, thereby implementing functions corresponding to programs. In other words, the processing circuitry under the state having read programs has the functions of the acquiring circuitry, the reference frame generating circuitry and the tracking processing circuitry. In addition, although as described above, the case in which the acquiring circuitry, the reference frame generating circuitry and the tracking processing circuitry in the medical image processing apparatus of the embodiments is implemented with single processing circuitry is explained, it is also possible to combine a plurality of separate processors to constitute the processing circuitry and implement functions of the acquiring circuitry, the reference frame generating circuitry and the tracking processing circuitry by processors executing programs.

Third Embodiment

In the foregoing embodiments, descriptions are given of cases in which the medical image processing apparatus 100 acquires ultrasound images captured by an ultrasound diagnosis apparatus and executes an image processing method are described. However, the image processing method may be executed by an ultrasound diagnosis apparatus. Accordingly, a case in which an ultrasound diagnosis apparatus executes an image processing method similar to those in the foregoing embodiments is described in a third embodiment.

FIG. 10 is a module diagram showing an exemplary configuration of an ultrasound diagnosis apparatus 300 according to the third embodiment. As shown in FIG. 10, the ultrasound diagnosis apparatus 300 according to the third embodiment includes an ultrasound probe 311, an input apparatus 312, a display 313, and an apparatus main body 320. The ultrasound probe 311 is communicably connected to transmitter receiver circuitry 321 described later, which is included in the apparatus main body 320. The input apparatus 312 and the display 313 are communicably connected to various circuitry included in the apparatus main body 320.

The ultrasound probe 311 is brought into contact with the body surface of the examined subject P and transmits and receives ultrasound waves. For example, the ultrasound probe 311 includes a plurality of piezoelectric transducer elements (referred to also as transducer elements). These piezoelectric transducer elements generate ultrasound waves based on transmission signals supplied from the transmitter receiver circuitry 321. The generated ultrasound waves are reflected in body tissue in the examined subject P and are received as reflected wave signals by the piezoelectric transducer elements. The ultrasound probe 311 transmits the reflected wave signals received by the piezoelectric transducer elements to the transmitter receiver circuitry 321.

The third embodiment can be applied to the ultrasound probe 311 whether the ultrasound probe 311 is a one-dimensional (1D) array probe that scans (two-dimensionally scans) a two-dimensional region inside the examined subject P or such a probe as a mechanical four-dimensional (4D) probe or a two-dimensional (2D) array probe that scans (three-dimensionally scans) a three-dimensional region inside the examined subject P.

The input apparatus 312 corresponds to a mouse, a keyboard, a button, a panel switch, a touch command screen, a foot switch, a track ball, a joystick, or the like. The input apparatus 312 receives various setting requests from an operator of the ultrasound diagnosis apparatus 300 and forwards the received various setting requests to the various circuitry in the apparatus main body 320 as appropriate.

The display 313 displays a graphical user interface (GUI) used by the operator for inputting various setting requests using the input apparatus 312 and displays, for example, images (ultrasound images) based on ultrasound image data generated by the apparatus main body 320.

The apparatus main body 320 is an apparatus that generates ultrasound image data based on the reflected wave signals received by the ultrasound probe 311. As shown in FIG. 10, the apparatus main body 320 includes, for example, the transmitter receiver circuitry 321, B-mode processing circuitry 322, Doppler processing circuitry 323, image generating circuitry 324, an image memory 325, memory circuitry 326 and processing circuitry 327. The transmitter receiver circuitry 321, the B-mode processing circuitry 322, the Doppler processing circuitry 323, the image generating circuitry 324, the image memory 325, the memory circuitry 326 and the processing circuitry 327 are communicably connected to one another.

The transmitter receiver circuitry 321 controls transmission and reception of ultrasound waves by the ultrasound probe 311. For example, the transmitter receiver circuitry 321 includes transmitter circuitry 321a and receiver circuitry 321b and controls transmission and reception of ultrasound waves by the ultrasound probe 311, based on instructions from the processing circuitry 327 described later. The transmitter circuitry 321a produces transmission waveform data and generates, from the produced transmission waveform data, transmission signals that the ultrasound probe 311 uses for transmitting ultrasound waves. The transmitter circuitry 321a then applies transmission signals to the ultrasound probe 311, thereby causing transmission of an ultrasound beam obtained by focusing ultrasound waves into a beam shape. The receiver circuitry 321b performs addition processing by assigning certain delay times to reflected wave signals received by the ultrasound probe 311, thereby generating reflected wave data in which reflection components from a direction agreeing with the reception directivity of the reflected wave signals are emphasized, and transmits the generated reflected wave data to the B-mode processing circuitry 322, the Doppler processing circuitry 323.

The B-mode processing circuitry 322 applies various kinds of signal processing to the reflected wave data generated by the receiver circuitry 321b from the reflected wave signals. The B-mode processing circuitry 322 applies, for example, logarithmic amplification and envelope detection processing to the reflected wave data received from the receiver circuitry 321b, thereby generating data (B-mode data) in which the signal intensity of each sample point (observation point) is expressed in brightness of luminance. The B-mode processing circuitry 322 transmits the generated B-mode data to the image generating circuitry 324.

In addition, the B-mode processing circuitry 322 performs signal processing for enabling harmonic imaging, which visualizes harmonic components. Known examples of harmonic imaging include contrast harmonic imaging (CHI) and tissue harmonic imaging (THI). Known examples of a scanning method for CHI and THI include amplitude modulation and phase modulation.

The Doppler processing circuitry 323 generates, from the reflected wave data received by the receiver circuitry 321b, data (Doppler data) into which pieces of motion information of a moving body based on the Doppler effect are extracted at sample points in a scanned region. Specifically, the Doppler processing circuitry 323 generates Doppler data into which average velocities, dispersion values, power values or the like are extracted as the pieces of motion information of the moving body at the respective sample points. Here, examples of the moving body include a blood flow, tissue of a cardiac wall or the like, and a contrast agent. The Doppler processing circuitry 323 transmits the generated Doppler data to the image generating circuitry 324.

The image generating circuitry 324 generates ultrasound image data from the data generated by the B-mode processing circuitry 322 and the Doppler processing circuitry 323. For example, the image generating circuitry 324 generates, from the B-mode data generated by the B-mode processing circuitry 322, B-mode image data in which the intensity of a reflected wave is expressed in luminance. The image generating circuitry 324 also generates Doppler image data representing moving body information from the Doppler data generated by the Doppler processing circuitry 323. The Doppler image data is velocity image data, dispersion image data, power image data, or image data obtained by combining any of the forgoing data.

The image memory 325 is a memory that stores therein data generated by the B-mode processing circuitry 322, the Doppler processing circuitry 323 and the image generating circuitry 324. For example, the image memory 325 stores therein the ultrasound image data generated by the image generating circuitry 324, in association with electrocardiographic waveforms of the examined subject P. When the amount of data to be stored in the image memory 325 exceeds the memory capacity of the image memory 325, relatively old data is deleted and updated.

The memory circuitry 326 is a storage apparatus that stores therein various kinds of data. For example, the memory circuitry 326 stores therein: control programs for performing transmission and reception of ultrasound waves, image processing and display processing; and various kinds of data such as diagnostic information (for example, patient IDs and doctor's findings), diagnosis protocols and various body marks. Data stored in the memory circuitry 326 can be transferred to an external apparatus via an interface unit (not illustrated).

In addition, the memory circuitry 326 stores therein data generated by the B-mode processing circuitry 322, the Doppler processing circuitry 323 and the image generating circuitry 324. For example, the memory circuitry 326 stores therein ultrasound image data corresponding to a certain number of heartbeats as specified by the operator. The memory circuitry 326 is one example of a memory unit that stores therein a plurality of images acquired by scanning the examined subject P for a certain time period.

The processing circuitry 327 controls all processing in the ultrasound diagnosis apparatus 300. Specifically, based on various setting requests input from the operator via the input apparatus 312 and various control program and various data loaded from the memory circuitry 326, the processing circuitry 327 controls processing in the transmitter receiver circuitry 321, the B-mode processing circuitry 322, the Doppler processing circuitry 323 and the image generating circuitry 324. The processing circuitry 327 causes the display 313 to display ultrasound image data stored in the image memory 325.

Furthermore, the processing circuitry 327 executes an acquiring function 327a, a reference frame generating function 327b and a tracking processing function 327c, as shown in FIG. 10. Here, for example, the memory circuitry 326 has processing functions to be executed by the components of the processing circuitry 327 shown in FIG. 10, namely, the acquiring function 327a, the reference frame generating function 327b and the tracking processing function 327c, recorded therein in the form of computer executable programs. The processing circuitry 327 is a processor for reading out and executing the programs from the memory circuitry 326, thereby implementing functions corresponding to the programs. In other words, the processing circuitry 327 includes the functions shown in the processing circuitry 327 in FIG. 10 only when having read out the programs. The acquiring function 327a is referred to also as an acquiring unit; the reference frame generating function 327b, a reference frame generating unit; and the tracking processing function 327c, a tracking processing unit. Details of the individual functions to be executed by the processing circuitry 327 will be described later.

When carrying out TCA analysis, the ultrasound diagnosis apparatus 300 configured as above executes ultrasound scanning in the presence of a contrast agent to capture ultrasound images. Subsequently, the ultrasound diagnosis apparatus 300 executes the following image processing method when tracking for example, the ROI that is a tumor region in ultrasound images captured in time series. The image processing method that the ultrasound diagnosis apparatus 300 executes may be executed with ultrasound images acquired in real time, or may be executed with ultrasound images that has been saved in a certain memory unit after ultrasound scanning and read out.

The acquiring function 327a executes the same function as the acquiring circuitry 101 according to the first embodiment. For example, the acquiring function 327a acquires a plurality of frames representing ultrasound images starting with an initial frame in time series.

The reference frame generating function 327b executes the same function as the reference frame generating circuitry 102 according to the first embodiment. For example, the reference frame generating function 327b compares the current frame and a previous frame to the current frame for determining the similarity therebetween, and generate a reference frame based on weighting processing on the previous frame and the initial frame using results of the comparison.

The tracking processing function 327c executes the same function as the tracking processing circuitry 103 according to the first embodiment. For example, the tracking processing function 327c carries out tracking processing between the reference frame and the current frame and between the current frame and the previous frame.

Modification of the Third Embodiment

In the third embodiment described above, the ultrasound diagnosis apparatus 300 is described as being configured to implement forward matching as in the case of the first embodiment. However, embodiments are not limited to this. For example, the ultrasound diagnosis apparatus 300 may be configured to implement forward matching and reverse matching as in the case of the second embodiment.

In this case, the acquiring function 327a executes the same function as the acquiring circuitry 101 according to the first embodiment. Likewise, the reference frame generating function 327b executes the same function as the reference frame generating circuitry 102 according to the first embodiment. The tracking processing function 327c executes the same function as the tracking processing circuitry 203 according to the second embodiment.

For example, the tracking processing function 327c implements forward matching and reverse matching both in matching between the reference frame and the current frame and in matching between the current frame and the previous frame. The forward matching refers to matching from any one of the reference frame and the previous frame as other frames to the current frame, while the reverse matching refers to matching from the current frame to the other frames. Here, when implementing forward matching between the reference frame and the current frame, the tracking processing function 327c sets the ROI in the reference frame before the matching as the corresponding region. When implementing forward matching between the current frame and the previous frame, the tracking processing function 327c sets the ROI in the previous frame before the matching as the corresponding region. When implementing forward matching between the reference frame and the current frame, the tracking processing function 327c sets the matched region in the reference frame after the reverse matching thereto from the current frame as the corresponding region. When implementing reverse matching between the current frame and the previous frame, the tracking processing function 327c sets the matched region in the previous frame after implementing the reverse matching thereto from the current frame as the corresponding region.

Other Embodiment

The embodiment is not limited to the embodiments described above.

In the embodiments described above, tracking is described as being to be implemented among three frames, that is, between the current frame and the reference frame and between the current frame and the previous frame. However, the embodiments are not limited to this. For example, tracking processing may be implemented between two frames that are, for example, the current frame and the reference frame. A description is given below of a case in which tracking processing between two frames is implemented in the medical image processing apparatus 200 according to the second embodiment. However, tracking processing between two frames can be similarly implemented in the ultrasound diagnosis apparatus 300 according to the third embodiment.

The tracking processing circuitry 203 implements tracking processing between the reference frame and the current frame. For example, the matching circuitry 204 in the tracking processing circuitry 203 implements tracking processing between the reference frame and the current frame.

Here, the matching circuitry 204 in the tracking processing circuitry 203 implements forward matching and reverse matching between the reference frame and the current frame. The forward matching refers to matching from the reference frame to the current frame, while the reverse matching refers to matching from the current frame to the reference frame. For example, the matching circuitry 204 in the tracking processing circuitry 203 sets, in the forward matching, the ROI in the reference frame before the matching as the corresponding region, and sets, in the reverse matching, the matched region in the reference frame after the reverse matching thereto from the current frame as the corresponding region.

Subsequently, based on a matched region in the current frame, the tracking result determining circuitry 205 in the tracking processing circuitry 203 calculates a variation amount between the matched region in the current frame and a region in the reference frame corresponding to the matched region. Here, the tracking result determining circuitry 205 in the tracking processing circuitry 203 calculates, as the variation amount, a differential between a region variation amount from the reference frame to the current frame and a region variation amount from the current frame to the reference frame.

The tracking result determining circuitry 205 in the tracking processing circuitry 203 then determines, when the calculated variation amount is smaller than a threshold, that the tracking is successful, and, when the variation amount is greater than or equal to the threshold, that the tracking is unsuccessful.

Optionally, the tracking processing circuitry 203 may include rejection processing circuitry configured to: discard the current frame when the tracking result determining circuitry 205 determines tracking to be unsuccessful; and retain the current frame when the tracking result determining circuitry 205 determines tracking to be successful.

In the embodiments described above, descriptions have been given of cases in which both forward matching and reverse matching are implemented between two frames. However, embodiments are not limited to this. For example, the tracking processing circuitry 203 may be configured to implement only forward matching between two frames.

The term "processor" used in the foregoing descriptions means, for example, a central processing unit (CPU), a graphics processing unit (GPU), or a circuit such as an application specific integrated circuit (ASIC) or a programmable logic apparatus (examples of which include a simple programmable logic apparatus (SPLD), a complex programmable logic apparatus (CPLD) and a field programmable gate array (FPGA)). The processor implements a function by reading out and executing a program stored in memory circuitry. Instead of being stored in memory circuitry, the program may be configured to be embedded directly in circuitry of the processor. In this case, the processor implements the function by reading out and executing the program embedded in the circuitry. Each processor in the present embodiments is not limited to being configured as a single circuit for that individual processor, and may be configured as a plurality of independent circuits combined into one processor to implement the function thereof. Furthermore, a plurality of components in FIG. 1, FIG. 4 and FIG. 10 may be integrated into one processor to implement the functions thereof.

In the description of the embodiments described above, each constituent element of each apparatus illustrated in the drawing is functional and conceptual, and it is not necessary to physically configure each apparatus as illustrated in the drawing. In other words, a specific form of separation/integration of each apparatus is not limited to that illustrated in the drawing, and the whole or a part of each apparatus may be functionally or physically distributed/integrated in an arbitrary unit in accordance with various loads, the use status, and the like. In addition, the entirety or an arbitrary part of each processing function performed in each apparatus may be realized by a CPU and a program that is interpreted and executed by the CPU or may be realized by hardware using a wired logic.

In addition, the control method described in the embodiments described above may be realized by executing a control program prepared in advance using a computer such as a personal computer or a workstation. This control program may be distributed through a network such as the Internet. In addition, this control program may be recorded on a computer-readable recording medium such as a hard disk, a flexible disk (FD), a CD-ROM, an MO, or a DVD and can be executed by being read by a computer from the recording medium.

According to at least one of the embodiments described above, it is possible to accurately track the ROI.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound diagnosis apparatus, comprising:
processing circuitry configured to
acquire a plurality of frames representing ultrasound images starting with an initial frame in time series;
compare a current frame and a previous frame to determine similarity therebetween, and generate a reference frame based on weighting processing on the initial frame and the previous frame using results of the similarity comparison; and
implement tracking processing between the reference frame and the current frame,
wherein the processing circuitry is further configured to implement the similarity comparison to increase a weight for the previous frame when the determined similarity is high and increase a weight for the initial frame when the determined similarity is low, and add the initial frame and the previous frame, which are subjected to the weighting processing, to generated the reference frame.

2. The ultrasound diagnosis apparatus according to claim 1, wherein
the initial frame is a frame set with a region of interest, and
the processing circuitry is further configured to displace a position of the region of interest in the previous frame with respect to a region of interest in the initial frame before the adding.

3. The ultrasound diagnosis apparatus according to claim 1, wherein the processing circuitry is further configured to implement the tracking processing between the current frame and the previous frame.

4. The ultrasound diagnosis apparatus according to claim 3, wherein the processing circuitry is further configured to
perform matching between the reference frame and the current frame and between the current frame and the previous frame; and
calculate a first variation amount between a region in the current frame matched with the reference frame and a region in the reference frame corresponding to the matched region, calculate a second variation amount between a region in the current frame matched with the previous frame and a region in the previous frame corresponding to the matched region, determine, when the calculated first variation amount and the calculated second variation amount are both smaller than a threshold, that the tracking is successful, and, when at least one of the first variation amount and the second variation amount is greater than or equal to the threshold, determine that the tracking fails.

5. The ultrasound diagnosis apparatus according to claim 4, wherein the processing circuitry is further configured to
implement forward matching and reverse matching both in the matching between the reference frame and the current frame and in the matching between the current frame and the previous frame, the forward matching referring to matching from any one of the reference frame and the previous frame as other frames to the current frame, and the reverse matching referring to matching from the current frame to the other frames; and
calculate, as the first variation amount, a differential between a region variation amount from the reference frame to the current frame and a region variation amount from the current frame to the reference frame, and calculate, as the second variation amount, a differential between a region variation amount from the previous frame to the current frame and a region variation amount from the current frame to the previous frame.

6. The ultrasound diagnosis apparatus according to claim 5, wherein the processing circuitry is further configured to,
when implementing the forward matching between the reference frame and the current frame, set a region of interest in the reference frame before the matching as the corresponding region,
when implementing the forward matching between the current frame and the previous frame, set a region of interest in the previous frame before the matching as the corresponding region,
when implementing the reverse matching between the reference frame and the current frame, set a matched region in the reference frame after the reverse matching thereto from the current frame as the corresponding region, and
when implementing the reverse matching between the current frame and the previous frame, set a matched region in the previous frame after the reverse matching thereto from the current frame as the corresponding region.

7. The ultrasound diagnosis apparatus according to claim 4, wherein the processing circuitry is further configured to discard the current frame when it is determined that the tracking fails, and retain the current frame when it is determined that the tracking is successful.

8. The ultrasound diagnosis apparatus according to claim 1, wherein the processing circuitry is further configured to
perform matching match between the reference frame and the current frame; and
calculate a variation amount between a matched region in the current frame and a region in the reference frame corresponding to the matched region, based on the matched region in the current frame, and determine, when the calculated variation amount is smaller than a threshold, that the tracking is successful, and, when the calculated variation amount is greater than or equal to the threshold, determine that the tracking fails.

9. The ultrasound diagnosis apparatus according to claim 8, wherein the processing circuitry is further configured to
implement forward matching and reverse matching between the reference frame and the current frame, the forward matching referring to matching from the reference frame to the current frame, the reverse matching referring to matching from the current frame to the reference frame; and
calculate, as the variation amount, a differential between a region variation amount from the reference frame to the current frame and a region variation amount from the current frame to the reference frame.

10. The ultrasound diagnosis apparatus according to claim 9, wherein the processing circuitry is further configured to set, in the forward matching, a region of interest in the reference frame before the matching as the corresponding region, and set, in the reverse matching, a matched region in the reference frame after the reverse matching thereto from the current frame as the corresponding region.

11. An image processing apparatus, comprising:
processing circuitry configured to
acquire a plurality of frames representing ultrasound images starting with an initial frame in time series;
compare a current frame and a previous frame to the current frame for determining similarity therebetween, and generate a reference frame based on weighting processing on the initial frame and the previous frame using results of the comparison; and
implement tracking processing between the reference frame and the current frame,
wherein the processing circuitry is further configured to implement the similarity comparison to increase a weight for the previous frame when the determined similarity is high and increase a weight for the initial frame when the determined similarity is low, and add the initial frame and the previous frame, which are subjected to the weighting processing, to generated the reference frame.

12. An image processing method, comprising:
acquiring a plurality of frames representing ultrasound images starting with an initial frame in time series;

comparing a current frame and a previous frame to determine similarity therebetween by implementing the similarity comparison to increase a weight for the previous frame when the determined similarity is high and increase a weight for the initial frame when the determined similarity is low, and generating a reference frame based on weighting processing on the initial frame and the previous frame using results of the comparison by adding the initial frame and the previous frame, which are subjected to the weighting processing; and implementing tracking processing between the reference frame and the current frame.

\* \* \* \* \*